United States Patent [19]

Gruner et al.

[11] 4,219,399

[45] Aug. 26, 1980

[54] INTERNALLY, ELECTRICALLY HEATED ELECTROCHEMICAL SENSING ELEMENT

[75] Inventors: Heiko Gruner, Stuttgart; Franz Rieger, Aalen-Wasseralfingen; Rainer Schüssler, Bietigheim, all of Fed. Rep. of Germany

[73] Assignee: Robert Bosch GmbH, Stuttgart, Fed. Rep. of Germany

[21] Appl. No.: 74,125

[22] Filed: Sep. 10, 1979

[30] Foreign Application Priority Data

Sep. 26, 1978 [DE] Fed. Rep. of Germany ....... 2841771

[51] Int. Cl.³ .......................................... G01N 27/58
[52] U.S. Cl. ................................................. 204/195 S
[58] Field of Search ........................... 204/195 S, 1 S; 123/119 E; 60/276

[56] References Cited

U.S. PATENT DOCUMENTS

| | | | |
|---|---|---|---|
| 3,546,086 | 12/1970 | Sayles | 204/195 S |
| 3,645,875 | 2/1972 | Record et al. | 204/195 S |
| 3,691,023 | 9/1972 | Ruka et al. | 204/1 T |
| 3,891,529 | 6/1975 | Beesch | 204/195 S |
| 4,019,974 | 4/1977 | Weyl et al. | 204/195 S |
| 4,155,827 | 5/1979 | Maurer et al. | 204/195 S |
| 4,169,778 | 10/1979 | Mann et al. | 204/195 S |
| 4,175,019 | 11/1979 | Murphy | 204/195 S |

FOREIGN PATENT DOCUMENTS

2732743  2/1979 Fed. Rep. of Germany ....... 204/195 S
1541208  2/1979 United Kingdom .

Primary Examiner—G. L. Kaplan
Attorney, Agent, or Firm—Frishauf, Holtz, Woodward & Goodman

[57] ABSTRACT

To provide a pre-heated sensor which is capable of heating the sensing element exposed to gases to a temperature of above 400° C. and preferably above 500° C., at which temperature the sensor will be essentially immune to lead content in the gases, an elongated heating rod is placed within a sensor structure in which a solid electrolyte tube is held in position by a first stressed compression spring, the heating rod being formed with a radially projecting flange against which a second compression spring bears, concentrically located within the first, the heating rod itself comprising a long ceramic tube, preferably formed with two longitudinal bores to accept connecting wires to a thermocouple positioned at the end of the tube to sense the temperature of the sensing tube, surrounded by a first metallic tube forming an electrical connection to one terminal of a spiral heating wire which is wrapped around a fiberglass sleeve slipped over the metallic tube, connected to a second metallic tube outside of the fiberglass sleeve which, in turn, has yet another fiberglass sleeve slipped thereover, which is split in the region of the flange, to provide a sensing element in which all components are concentrically located within each other, and held in position by an end cap and in place by compression springs to permit assembly from the region of the end cap which, upon completion of the assembly, is secured in position, and compression-stressing the springs, thereby providing reliable connection and shock and vibration resistant seating of all components while permitting simple assembly under mass production conditions.

10 Claims, 1 Drawing Figure

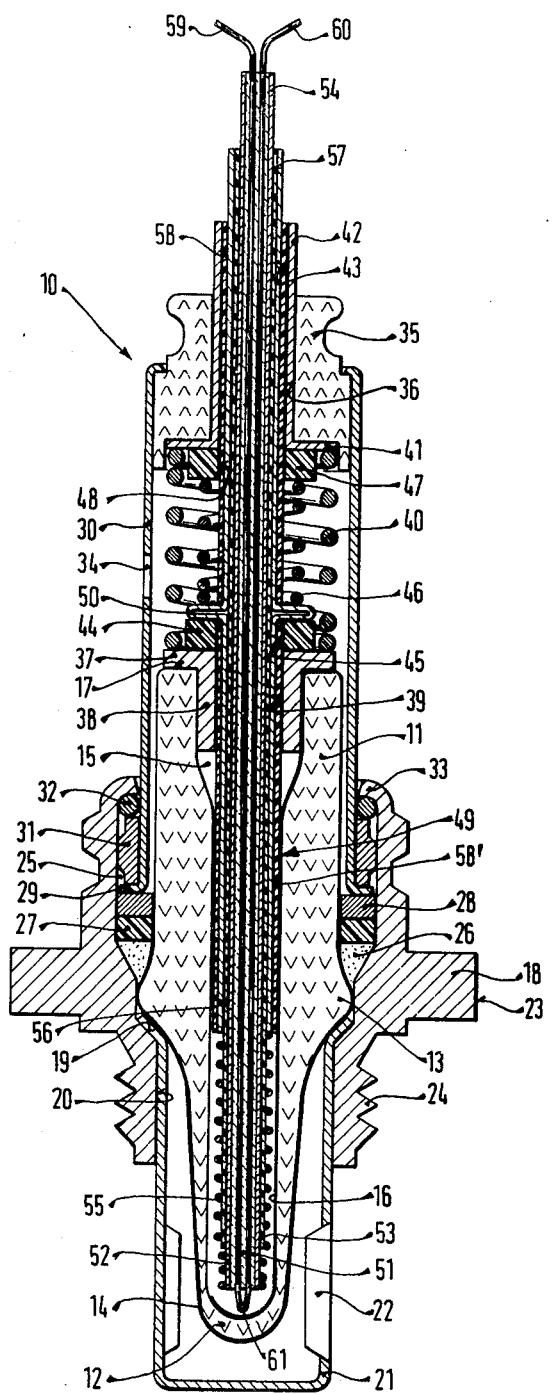

INTERNALLY, ELECTRICALLY HEATED ELECTROCHEMICAL SENSING ELEMENT

The present invention relates to an electrochemical sensing element to determine the oxygen content of a test gas, particularly the oxygen content of exhaust gases from internal combustion engines, which is supplied with an electrical heating element to raise the temperature of the sensing element.

BACKGROUND AND PRIOR ART

Various types of electrochemical sensing elements are known; one such sensor has an ion conductive solid electrolyte which, however, to provide useful sensing output function, is operative only when its temperature is above about 400° C. Only then will it have sufficient ion conductivity to permit its practical use. If the test gases, for example the exhaust gases of an internal combustion engine, contain lead, then the temperature may have to be raised to above 500° C. before the output signal from the sensor will be essentially independent of the lead content in the gas. The output signals of such sensors are, additionally, highly dependent on the temperature of the solid electrolyte itself.

It is desirable to decrease the response time of such sensors when exposed to cool gases, in order to obtain an output signal which can be readily evaluated. It is also desirable to increase the lifetime of such sensors, particularly when exposed to exhaust gases which contain lead, and further to increase the accuracy of measurement, when exposed to such lead-containing gases. To improve the operation of such sensors, then, it is desirable to provide controlled heating elements for the sensors. Controlled heating elements are also desirable if such sensors are located in the exhaust system of the internal combustion engine at locations in which the exhaust gases are already quite cool.

A sensor of the type to which the present invention relates is described in U.S. Pat. No. 3,546,086; this sensor has a solid electrolyte tube, closed at one end, within which a resistance heating element and a temperature sensing element are located. Such sensors, while operating satisfactorily, are expensive to manufacture, particularly under high volume conditions, and are difficult to make in mass production. There is always room for increasing the shock and vibration resistance of such sensors. Other types of sensors to which the present invention can be applied are electrochemical sensors with ion conductive solid electrolyte on which a protective layer is applied at the side facing the test gases—typically exhaust gases from an internal combustion (IC) engine, and on which further an electron conductive catalyzing layer is provided. Such sensors are described, for example, in U.S. Pat. No. 3,645,875. The sensors may, additionally, be supplied with a diffusion layer which limits the current of the sensor, see, for example, U.S. Pat. No. 3,691,023, U.S. application Ser. No. 6,093, filed Jan. 24, 1979, DIETZ (Continuation-in-Part of U.S. Ser. No. 885,368, filed Mar. 13, 1978, now abandoned).

THE INVENTION

It is an object to provide a sensor which is essentially immune to vibration or shock, which provides an adequate output signal suitable for evaluation even if exposed to test gases of comparatively low temperature, and containing lead.

Briefly, the general construction of the sensor is similar to that described in U.S. Pat. No. 3,546,086; in accordance with the invention, a heating rod, which preferably contains a spirally coiled heating wire therein, is formed with a mounting flange intermediate its length, of electrically conductive material, and projecting radially from the heating rod; the mounting flange is secured within the sensor by a compression spring which is fitted within another compression spring which holds the tubular ion conductive sensing element in place, with sufficient space to provide for insulation between the two compression springs. The entire sensor is located within a socket which is arranged to accept the compression forces of the respective springs, and insulating bushings are located within the socket to insulate the springs from each other at the points where they bear against the cap. Electrical connection to the heating wire within the heating rod is made by mutually insulated elongated conductive elements, for example telescopic interfitting tubes, extending essentially parallel to the electrode connection elements which, likewise, may be an elongated tube, or a centrally positioned rod, to provide electrical connection to the heating terminals. Connection leads to a temperature sensing element, preferably located at the bottom of the closed tube, can also be provided, for example in the form of fine holes, through which the thin sensing wires to a thermocouple can be threaded.

The sensor in accordance with this construction has the advantage that the ion conductive sensing element, the heating element and, if provided, the thermocouple and its connection, are all fitted together in a single sturdy vibration and shock-free unit which can be constructed in mass production by fitting longitudinally concentric elements within each other; the cost of such sensors, thus, can be substantially reduced. The construction of the sensor is such that it can be used both with a heater and with a thermocouple-type temperature sensing element; it can be used, however, also without the temperature sensing element, if this is not needed. The construction, additionally, has the advantage that it can be assembled of components which are readily available and are standard articles of commerce, so that special productions runs for specific items to assemble the sensor are not needed.

Drawings, illustrating a preferred example, wherein the single figure is a longitudinal cross-sectional view through the sensor, to an enlarged scale, and illustrating a unit which includes both a heating element as well as a temperature sensing unit.

The sensor 10 which, in cross section is essentially circular, has an ion conductive solid electrolyte tube 11, consisting of stabilized zirconium dioxide or other material which is ion conductive. The lower end—with respect to the figure—is intended for extension within the exhaust system of an internal combustion engine, for example to be fitted in the exhaust pipe. The closed bottom 12 will be exposed to the exhaust gases. The external portion of the tube 11 is formed with a radially projecting flange 13. The tube 11 is coated at its outer surface with an electron conductive, porous catalyzing layer 14, typically of platinum, which at least in part covers the portion of the sensor exposed to the exhaust gases, and at least a portion of the flange 13 of the tube 11. A protective layer can be applied to the catalyzing layer 14—not shown—to protect the sensor and the layer 14 against mechanical and thermal attack by the exhaust gases. Reference is made to U.S. Pat. No.

3,645,875 which describes the sensor in general; U.S. Pat. No. 3,691,023 and the aforementioned application Ser. No. 6,093, filed Jan. 24, 1979, DIETZ, contain additional discussion and illustration of the diffusion layer which, therefore, has been omitted from the drawing of the present application, for clarity, since its structure and operation are known.

The solid electrolyte tube 11 has an electron conductive path 16 applied at the inner surface 15. The path 16 extends down to the bottom 12 and forms a contact surface; path 16, also, may consist of platinum. At the upper end of the sensor, the path 16 extends up and over the facing surface 17 of the solid electrolyte tube 11.

The solid electrolyte tube 11 is located in a housing or socket 18 which, preferably, is electrically conductive and, for example, may consist of heat-resistant steel. It may form, for example, one of the terminals for the sensing signal of the sensor 10. The socket 18 has an internal bore or opening 20, with a constricting shoulder. A protective tube 21, likewise of metal, and formed with openings to permit gases to pass therethrough, as shown schematically at 22, is fitted against the internal shoulder. The flange 13 of the solid electrolyte tube 11 fits against the shoulder formed by the protective tube 21 and clamps the tube 21 against the housing 18. The protective tube 21 is spaced from the sensing end of the solid electrolyte tube 11. The housing or socket 18 at the outside is formed with a hexagonal socket fit, similar to a spark plug, and with a thread 24 to permit seating the socket 18 in a suitably tapped opening in the exhaust system of an IC engine. A ring-shaped gap of greater diameter than the diameter of the tube 11 is formed between the housing 18 and the outer surface of the tube 11 beyond the flange. The area immediately above the flange of this ring-shaped gap is filled with an electrically conductive sealing mass 26, for example graphite powder, which contacts the catalyzing layer 14 on the solid electrolyte tube as well as the metallic housing 18. The sealing mass 26 is tapped together and held in place by an insulating bushing or washer 27, against which a metallic washer 28 is seated. The metallic washer 28 is in engagement with an externally peened-over edge or flange 29 of a protective tube 30, preferably of metal, such as brass, steel, or the like. The upper edge of the flange 29 is held in position by a spacer bushing 31, over which a metal ring 32 of circular cross-section is placed. The housing 18 is peened or flanged inwardly over the metal ring 32, as seen at 33, to compress the metal ring 32, bushing 31, flange 29, metal bushing 28, insulating bushing 27 and the graphite sealing mass 26, and thus hold the solid electrolyte tube 11 with its flange 13 securely seated within the housing, even in the presence of vibration or shock.

The protective tube 30 is a metallic tubular element which extends upwardly (with respect to the figure) over the terminal-end portion of the solid electrolyte tube 11. It is formed with at least one air admission opening 34, to permit ambient air, the oxygen of which forms a reference oxygen gas, to penetrate into the interior of the sensing tube 11. The upper terminal end of the protective tube 30 secures an insulating cap 35 in position. Cap 35 is formed with a longitudinal bore 36 which is coaxial with respect to the interior 15 of the solid electrolyte tube 11.

The upper facing end surface 17 of the solid electrolyte tube forms the upper terminal of the conductive path 16, in the interior of the tube 11. The flange 37 of a longitudinally slit contact element 38 is seated on the end surface 17. The contact element 38 extends into the interior of the solid electrolyte tube 15 to form a guide bushing. It, in turn, is formed with a central opening or bore 39. A compression spring 40, held under compression, bears against the flange 37 at the side remote from the solid electrolyte tube 11. The upper end of the compression spring 40 bears against a second connection element 42 which extends through the central bore 36 of the insulating cap 35. The second connection element 42 is formed with a flange 41 against which the spring 40 can bear. The element, further, is formed with a central bore 43. The first compression spring 40 is spaced within the interior of the protective tube 30 and forms the electrical connection between the contact element 38 and the second contact element 42 which, together with the housing 18, form the two electrical output terminals for the output signal from the sensor formed by the solid electrolyte tube 11 and the electrodes 14, 16 thereon.

The general construction of the sensors so far described is similar to the sensor of U.S. Pat. No. 3,891,529.

In accordance with the present invention, a heating rod is concentrically fitted within the sensor construction so far described, to permit concentric placement of elements and ready assembly by fitting the parts within each other, suitably guided in guide bushings and guide elements to maintain the respective spacial relationship relative to each other, and prevent electrical contact, where undesired, while additionally forming electrical contact elements, where constructed to do so. As will appear, the construction of the sensor is such that the elements can be fitted concentrically within each other, the subassembly of solid electrolyte tube 11, with the elements therein, as well as the projecting springs and connecting elements thereon, then being assembled to the socket, into which the protective tube 21 has been fitted by placing the subassembly within the socket so that the flange 13 will bear against its respective shoulder. The socket flange 33 can then be closed, and the cap 35 pushed down, thus compressing springs 40 and an inner spring 46—as will appear—and permitting closing off of tube 30 by rolling over the upper edge against the respectively formed shoulder on the cap 35. Mass production of the sensor, together with the heating element and a temperature sensor—if desired—thus is readily possible.

The following elements and parts are located concentrically within the compression spring 40 and the first and second connection or contact elements 38, 42: a first insulating washer 44, engaging the contact element 38 and providing, further, for centering of the spring 40; a second compression spring 46, spaced from the first compression spring 40 and electrically isolated therefrom; a second insulating washer 47, engaged on the flange 41 of the second connecting element 42; a heating rod 49. The bushings 44, 47 are formed with respective central bores 45, 48. The second compression spring 46 is also mechanically stressed, that is, is under compression, and concentrically surrounds the heating rod 49. Heating rod 49 extends through the central bore 43 of the second connecting element 42, through the contact element 38 and into the interior 15 of the solid electrolyte tube 11. It is guided and held in position by the central bores 43 and 39 of the respective connecting elements 42, 38, and is held in axial position by the second compression spring 46. The longitudinal position of the heating rod 49, in accordance with a feature of the invention, is determined by a locating flange 50 which is held in position by the compression spring 46. As shown, and in a preferred embodiment, the flange 50 is clamped by the spring 46 against the insulating bushing 44, and electrically isolated from the first compression spring 40. The flange could, however, also be formed to be placed against the insulating bushing 47, and held thereagainst by the compression spring 46 which then would bear directly against the insulating bushing 44, and hold the flange against the bushing 47 instead, at the upper end of the spring 46.

The heating rod 49 has an electrically insulated, rod-like carrier 51, preferably of ceramic material, and coaxially fitted within a first metallic tube 52. One end of the rod-like, preferably ceramic carrier 51 extends close to the bottom 12 of the solid electrolyte tube 11; the other end portion of the rod 51 extends from the second connecting element 42 of the sensor 10, axially outwardly thereof. An insulating jacket 53 is located on the metallic tube 52, leaving a small projection of the metallic tube 52 from the insulating jacket 53. Preferably, the insulating jacket 53 is made of woven fiberglass tubing or sleeve material; the insulating sleeve 53 does not cover the end portion of the metallic tube 52 extending within the solid electrolyte tube 11 and leaves, also at the upper or terminal end, a small region to form a first connection 54 for a heater element 55. The heater element 55 is positioned within the interior space 15 of the solid electrolyte tube in the region surrounded by the protective tube 21, and is spirally wound about the insulating sleeve or jacket 53. The heater element 55 is welded to the metallic tube 52 adjacent the lowermost end thereof. The connecting end of the heater element 55, that is, the upper end in the figure, is connected to a second metallic tube 56 which is located above the insulating jacket or sleeve 53 and, at the connection end, extends from the second connecting portion or terminal 42. The portion of the metallic tube 56 which extends from the second connecting element 42 forms the second heating terminal 57. The outside of the second metallic tube 56 is formed with the flange 50 of the heating rod 49, that is, is formed with the flange which locates the heating rod in position. At both sides of the flange 50, a second insulating jacket or sleeve 58, 58', respectively, is located, which may also be a woven fiberglass sleeve or fiberglass tubing. The second insulating sleeve 58, 58', respectively, extends within a portion of the interior space 15 in the solid electrolyte tube and engages the interior wall thereof throughout a portion of its length. Sleeve 58' extends within the central bore 39 of the contact portion, within the central bore 45 of the first insulating bushing 44; the sleeve 58 extends through the central bore 48 of the second insulating bushing 47 and in the central bore 43 of the second connecting element 42. The sleeve 58, 58', respectively, has a wall thickness which is so selected that the heater element 55 will not be in electrical contact with the conductive path 16 within the interior 15 of the solid electrolyte tube 11. The tube 56 can be deformed in the region of the second heating terminal 57 to thereby fix the respective elements of the heating rod 49 in position relative to each other.

The ceramic rod 51 is formed with two longitudinal bores—not numbered in the drawing for ease of analysis—in which respective connecting wires 59, 60 for a temperature sensor 61 are positioned. The connecting wires 59, 60 extend from the end portion of the ceramic rod 51 and are connected to a thermocouple which forms the temperature sensor 61. The temperature sensor 61 and the two connecting wires 59, 60 are insulated both with respect to the conductive path 16 as well as the current carrying portions of the heater element 55.

Sensors of this type can be used to provide an output signal representative of the presence or absence of oxygen in test gases, typically in exhaust gases of internal combustion engines; they may, however, also be used in other applications. For example, they can be used in the induction or inlet tube or inlet manifold of internal combustion engines to extend and sense the oxygen composition of the air-fuel mixture. British Pat. No. 1,541,208 (to which German DE-OS No. 27 44 844 corresponds) describes a system in which an ion conductive solid electrolyte sensor is positioned in sensing relationship to the supply fuel-air mixture to an internal combustion engine. The sensor may, also, be used with other applications, in which the oxygen content of a test gas is to be sensed.

Various changes and modifications may be made within the scope of the inventive concept.

We claim:

1. Electrically heated electrochemical sensing element to determine the oxygen content of a test gas, particularly exhaust gases from internal combustion engines, having
    an ion conductive solid electrolyte tube (11) closed at one end, the outside of which is adapted to be exposed to the test gas and the inside to a reference gas, such as air;
    a porous, conductive catalyzing layer (14) at least on a portion of the outside of said ion conductive tube and exposed to the test gas and an electrically conductive path extending for at least a portion along the length of the tube and electrically connected thereto;
    an electrically conductive path (16) at the inside of the tube;
    a housing or socket (18);
    means (13; 26, 27, 28, 29, 31, 32, 33) securing said tube (11) in the socket;
    means (17, 34, 40, 41, 42) providing an external electrical connection to at least one of said paths, and including a first compression spring (40) and an elongated electrode connection element (42) extending outside of the socket and insulated therefrom;
    an internal heating rod (49) extending into the interior of the tube adjacent the closed end thereof, and positioned centrally within the compression spring (40);
    and means securing the heating rod within the solid electrolyte tube (11)
    comprising, in accordance with the invention,
    a mounting flange (50) projecting radially from the heating rod intermediate the length thereof;
    a second compression spring (46) of smaller diameter than said first spring (40) bearing against said flange and located within said first spring;
    cap means (35) secured to the socket and accepting the compressive forces of said springs (40, 46);
    insulating bushings (44, 47) electrically insulating said springs from each other;
    and mutually insulated elongated conductive elements (52, 56) extending axially parallel to the electrode connection element and forming external heating connection terminals for said heating rod (49).

2. Sensing element according to claim 1, wherein said electrical connection means connected to at least one of said paths (14, 16) comprises a tube (42) formed with a flange (41) against which said first compression spring (40) bears to make electrical contact therewith.

3. Sensing element according to claim 1, wherein said mutually insulated elongated conductive elements (52, 56) comprise concentrically arranged tubes.

4. Sensing element according to claim 3, wherein said electrical connection means connected to at least one of said paths (14, 16) comprises a tube (42) formed with a flange (41) against which said first compression spring (40) bears to make electrical contact therewith;

and wherein all said tubes are concentric and insulated from each other.

5. Sensing element according to claim 1, wherein the heating rod (49) comprises an elongated rod-like carrier (51) of insulating material;

a metallic tube (52) positioned thereon;

an insulating sleeve (53) located on the metallic tube (52);

a spiral electrical resistance heating wire electrically connected to said metallic tube (52) and wound over said insulating sleeve (53);

a second metallic tube (56) positioned over said insulating sleeve and having its end spaced from the end of said first tube, the electrical resistance heating wire being connected to said second metallic tube which forms a second electrical connection terminal therefor, said tubes forming said mutually insulated elongated conductive elements;

said mounting flange (50) being formed on said second, outer metallic tube (56);

and a second insulating sleeve (58, 58') surrounding the outside of the second metallic tube.

6. Sensing element according to claim 5, wherein said second insulating sleeve is a two-part sleeve (58, 58'), one part, each, being located at opposite sides of said flange.

7. Sensing element according to claim 5, wherein at least one of said insulating sleeves (53, 58, 58') of the heating rod comprises fiberglass fabric.

8. Sensing element according to claim 5, wherein said electrical connection means connected to at least one of said paths (14, 16) comprises a tube (42) formed with a flange (41) against which said first compression spring (40) bears to make electrical contact therewith;

and wherein all said tubes are concentrically arranged, and electrically insulated from each other.

9. Sensing element according to claim 5, further including two thermocouple connecting wires (59, 60) embedded in said elongated rod of insulating material (51) of the heating rod;

and a temperature sensing element (61) located adjacent the inner, closed end of said solid electrolyte tube (11) and connected to said sensing connection wires.

10. Sensing element according to claim 9, wherein said electrical connection means connected to at least one of said paths (14, 16) comprises a tube (42) formed with a flange (41) against which said first compression spring (40) bears to make electrical contact therewith;

wherein all said tubes are concentrically arranged, and electrically insulated from each other;

wherein said second insulating sleeve is a two-part sleeve (58, 58'), one part, each, being located at opposite sides of said flange;

and wherein at least one of said insulating sleeves (53, 58, 58') of the heating rod comprises fiberglass fabric.

* * * * *